US010638080B2

(12) United States Patent
Ovchinnikov et al.

(10) Patent No.: US 10,638,080 B2
(45) Date of Patent: Apr. 28, 2020

(54) SYSTEMS AND METHOD FOR AUGMENTED REALITY OPHTHALMIC SURGICAL MICROSCOPE PROJECTION

(71) Applicant: Novartis AG, Basel (CH)

(72) Inventors: Mikhail Ovchinnikov, Dana Point, CA (US); John Koontz, Chino, CA (US); Andrew Steven Hopper, Fort Worth, TX (US); Cesario Dos Santos, Newport Beach, CA (US)

(73) Assignee: ALCON INC. (CH)

( * ) Notice: Subject to any disclaimer, the term of this patent is extended or adjusted under 35 U.S.C. 154(b) by 21 days.

(21) Appl. No.: 15/878,910

(22) Filed: Jan. 24, 2018

(65) Prior Publication Data

US 2018/0220100 A1 Aug. 2, 2018

Related U.S. Application Data

(60) Provisional application No. 62/452,077, filed on Jan. 30, 2017.

(51) Int. Cl.
*H04N 5/445* (2011.01)
*A61B 90/20* (2016.01)
(Continued)

(52) U.S. Cl.
CPC ......... *H04N 5/44504* (2013.01); *A61B 90/20* (2016.02); *A61B 90/37* (2016.02);
(Continued)

(58) Field of Classification Search
CPC ........ G06F 3/147; G06F 3/013; G06F 3/0484; G06T 19/006; G02B 2027/014;
(Continued)

(56) References Cited

U.S. PATENT DOCUMENTS 6,370,224 B1 * 4/2002 Simon .................. A61B 6/5252
378/62
6,559,813 B1 * 5/2003 DeLuca ................. G02B 27/22
345/8

(Continued)

FOREIGN PATENT DOCUMENTS

WO 2008078320 A2 7/2008
WO 2016133644 A1 8/2016

*Primary Examiner* — Philip P. Dang
(74) *Attorney, Agent, or Firm* — Joseph Weatherbee, Esq.

(57) ABSTRACT

The disclosure provides a system including an augmented reality device communicatively coupled to an imaging system of an ophthalmic microscope. The augmented reality device may include a lens configured to project a digital image, a gaze control configured to detect a focus of an eye of an operator, and a dimming system communicatively coupled to the gaze control and the outer surface and including a processor that receives a digital image from the imaging system, projects the digital image on the lens, receives a signal from the gaze control regarding the focus of the eye of the operator, and transitions the outer surface of the augmented reality device between at least partially transparent to opaque based on the received signal. The disclosure further includes a method of performing ophthalmic surgery using an augmented reality device and a non-transitory computer readable medium able to perform augmented reality functions.

20 Claims, 3 Drawing Sheets

(51) Int. Cl.
*A61B 90/00* (2016.01)
*G06F 3/01* (2006.01)
*G06T 19/00* (2011.01)

(52) U.S. Cl.
CPC ............ *G06F 3/013* (2013.01); *G06T 19/006* (2013.01); *A61B 2090/365* (2016.02)

(58) Field of Classification Search
CPC ............. G02B 27/017; G02B 27/0093; G02B 2027/0187; G02B 2027/0138; G09G 2354/00; G09G 2380/08; A61B 90/20; A61B 90/37; A61B 34/25; A61B 2090/502; A61B 2090/365; A61B 2017/00216; H04N 5/44504
See application file for complete search history.

(56) References Cited

U.S. PATENT DOCUMENTS

| | | | | |
|---|---|---|---|---|
| 7,339,148 B2* | 3/2008 | Kawano | ............... | G02B 21/002 250/201.3 |
| 7,369,101 B2* | 5/2008 | Sauer | ................. | G02B 27/0101 345/629 |
| 7,376,903 B2* | 5/2008 | Morita | ................... | G06F 3/011 600/424 |
| 8,570,372 B2* | 10/2013 | Russell | ................... | G06F 3/013 348/136 |
| 8,777,413 B2* | 7/2014 | Zhou | ................... | A61B 3/1015 351/206 |
| 8,933,912 B2* | 1/2015 | Ambrus | ............. | G02B 27/0093 178/18.09 |
| 8,994,672 B2* | 3/2015 | Thorn | ................... | G06F 3/011 345/173 |
| 9,143,693 B1* | 9/2015 | Zhou | ................. | H04N 5/23293 |
| 9,358,103 B1* | 6/2016 | Wortz | ................... | A61F 2/1694 |
| 9,690,099 B2* | 6/2017 | Bar-Zeev | ............. | G02B 27/017 |
| 9,727,132 B2* | 8/2017 | Liu | ........................ | G06F 3/012 |
| 9,782,159 B2* | 10/2017 | Tesar | ....................... | A61B 1/05 |
| 9,787,977 B2* | 10/2017 | Bernard | ............ | G02B 27/2228 |
| 9,844,321 B1* | 12/2017 | Ekvall | ...................... | A61B 3/13 |
| 10,028,651 B2* | 7/2018 | Tesar | ................... | A61B 90/361 |
| 10,127,706 B2* | 11/2018 | Jones | ..................... | G06T 11/60 |
| 10,134,198 B2* | 11/2018 | Miller | ...................... | G06F 1/163 |
| 10,146,067 B2* | 12/2018 | Tsai | ........................ | G02C 7/10 |
| 10,162,412 B2* | 12/2018 | Nishizawa | ............. | G06F 3/013 |
| 10,182,714 B2* | 1/2019 | Eslami | ................. | A61B 5/7217 |
| 10,187,634 B2* | 1/2019 | Eash | ..................... | G02F 1/0136 |
| 10,238,279 B2* | 3/2019 | Izatt | .................... | G02B 21/0012 |
| 10,268,276 B2* | 4/2019 | Fisher | .................. | G02B 27/017 |
| 10,295,815 B2* | 5/2019 | Romanowski | ...... | G02B 21/0012 |
| 2006/0176242 A1* | 8/2006 | Jaramaz | ............... | A61B 5/0059 345/7 |
| 2008/0297535 A1* | 12/2008 | Reinig | ............... | G02B 27/2235 345/633 |
| 2012/0022408 A1* | 1/2012 | Hubschman | .......... | A61B 3/0025 600/587 |
| 2012/0038629 A1* | 2/2012 | Brown | ................... | A61B 3/113 345/419 |
| 2012/0068913 A1 | 3/2012 | Bar-Zeev et al. | | |
| 2012/0113092 A1 | 5/2012 | Bar-Zeev et al. | | |
| 2014/0160264 A1* | 6/2014 | Taylor | ................. | G02B 21/008 348/79 |
| 2014/0247199 A1* | 9/2014 | Vartanian | ........... | H04N 5/23206 345/8 |
| 2015/0278604 A1* | 10/2015 | Shuster | ............. | G06K 9/00671 345/8 |
| 2016/0155267 A1 | 6/2016 | Bean et al. | | |
| 2017/0007799 A1* | 1/2017 | Samec | .................. | A61B 3/085 |
| 2017/0143442 A1* | 5/2017 | Tesar | ..................... | A61B 90/37 |
| 2017/0256095 A1* | 9/2017 | Bani-Hashemi | ...... | G06T 19/006 |
| 2018/0048882 A1* | 2/2018 | Eash | ..................... | H04N 13/337 |
| 2018/0081429 A1* | 3/2018 | Akenine-Moller | ..... | G06F 3/011 |
| 2018/0122142 A1* | 5/2018 | Egeler | ................... | G06T 19/006 |
| 2018/0158390 A1* | 6/2018 | Sanglimsuwan | ....... | G09G 3/003 |
| 2019/0015167 A1* | 1/2019 | Draelos | ................ | A61B 34/25 |

* cited by examiner

SYSTEMS AND METHOD FOR AUGMENTED REALITY OPHTHALMIC SURGICAL MICROSCOPE PROJECTION

TECHNICAL FIELD

The present disclosure relates to ophthalmic surgery and surgical equipment, and more specifically, to systems for and methods for augmented reality ophthalmic surgical microscope projection.

DESCRIPTION OF THE RELATED ART

In ophthalmology, ophthalmic surgery is performed on the eye and accessory visual structures to save and improve the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make a tremendous difference in the patient's vision after the surgery.

Ophthalmic surgery is performed on the eye and accessory visual structures. During ophthalmic surgery, a patient is placed on a support, facing upward, under a surgical microscope. An eye speculum is inserted to keep the eye exposed. Surgeons often use a surgical microscope to view the patient's eye, and surgical instruments may be introduced to perform any of a variety of different procedures. The surgical microscope provides imaging and optionally illumination of parts of the eye during the procedure. A surgical microscope may be configured in many forms, for example, as a ceiling-mounted surgical microscope or a mobile, cart-mounted surgical microscope.

Microscopic images are used in ophthalmic surgeries to view small eye structures. Although they are magnified, how closely these images otherwise match what can be seen with normal vision impacts how well the surgery can be performed. Monocular microscopic images provide information about the object being viewed through size, focus, shadowing, and occlusion. Three dimensional (3D) displays have now added binocular disparity, the difference in how an image is seen by one eye as compared to the other, which makes them more realistic and provides additional visual information to the surgeon. However, there remains room for improvement in the information contained in microscopic images used in ophthalmic surgeries.

SUMMARY

The present disclosure provides a system for ophthalmic surgery. The system may include an augmented reality device communicatively coupled to an imaging system of an ophthalmic microscope. The augmented reality device may include a lens configured to project a digital image, an outer surface coupled to the lens, the outer surface being at least partially transparent, a gaze control configured to detect a focus of an eye of an operator of the augmented reality device and transmit a signal based on the focus, and a dimming system communicatively coupled to the gaze control and the outer surface. The dimming system may further include a processor operable to receive the digital image from the imaging system of the ophthalmic microscope, project the digital image on the lens, receive a signal from the gaze control regarding the focus of the eye of the operator, and transition the outer surface of the augmented reality device between at least partially transparent to opaque based on the received signal.

The system may further have one or more of the following additional features, which may be combined with one another unless clearly mutually exclusive: i) the augmented reality device may include augmented reality glasses; ii) the digital image may include a separate image projected on the lens for each eye of the operator; iii) the system may include an instrument configured to engage with the digital image; iii-a) the instrument may include a physical instrument manipulated by the operator; iii-b) the instrument may include a digital instrument manipulated by the operator; iv) the system may include a control device configured to engage with the digital image.

The present disclosure further provides a method of performing ophthalmic surgery. The method may include receiving a digital image from an imaging system of an ophthalmic microscope, projecting the digital image on a lens of an augmented reality device, receiving a signal regarding a focus of an eye of an operator, and transitioning an outer surface of the augmented reality device between at least partially transparent to opaque based on the received signal.

The method may further have one or more of the following additional features, which may be combined with one another unless clearly mutually exclusive: i) the augmented reality device may include augmented reality glasses; ii) the digital image may include a separate image projected on the lens for each eye of the operator; iii) the method may further include engaging an instrument with the digital image; iii-a) the instrument may include a physical instrument manipulated by the operator; iii-b) the instrument may include a digital instrument manipulated by the operator; iv) the method may include a control device configured to engage with the digital image.

The present disclosure further includes a non-transitory computer readable medium having instructions stored therein, the instructions readable by a processor and, when read and executed, configured to cause the processor to receive a digital image from an imaging system of an ophthalmic microscope, project the digital image on a lens of an augmented reality device, receive a signal regarding a focus of an eye of an operator, and transition an outer surface of the augmented reality device between at least partially transparent to opaque based on the received signal.

The non-transitory computer readable medium may further have one or more of the following additional features, which may be combined with one another unless clearly mutually exclusive, i) the augmented reality device may include augmented reality glasses; ii) the digital image may include a separate image projected on the lens for each eye of the operator; iii) the processor may be configured to engage an instrument with the digital image; iii-a) the instrument may include a physical instrument manipulated by the operator; iii-b) the instrument may include a digital instrument manipulated by the operator.

Any above system may include any above non-transitory computer readable medium and may carry out any above method. Any above non-transitory computer readable medium may also carry out any above method.

BRIEF DESCRIPTION OF THE DRAWINGS

For a more complete understanding of the present disclosure and its features and advantages, reference is now made to the following description, taken in conjunction with the accompanying drawings, which are not to scale, in which like numerals refer to like features, and in which.

DETAILED DESCRIPTION

Figure 1:
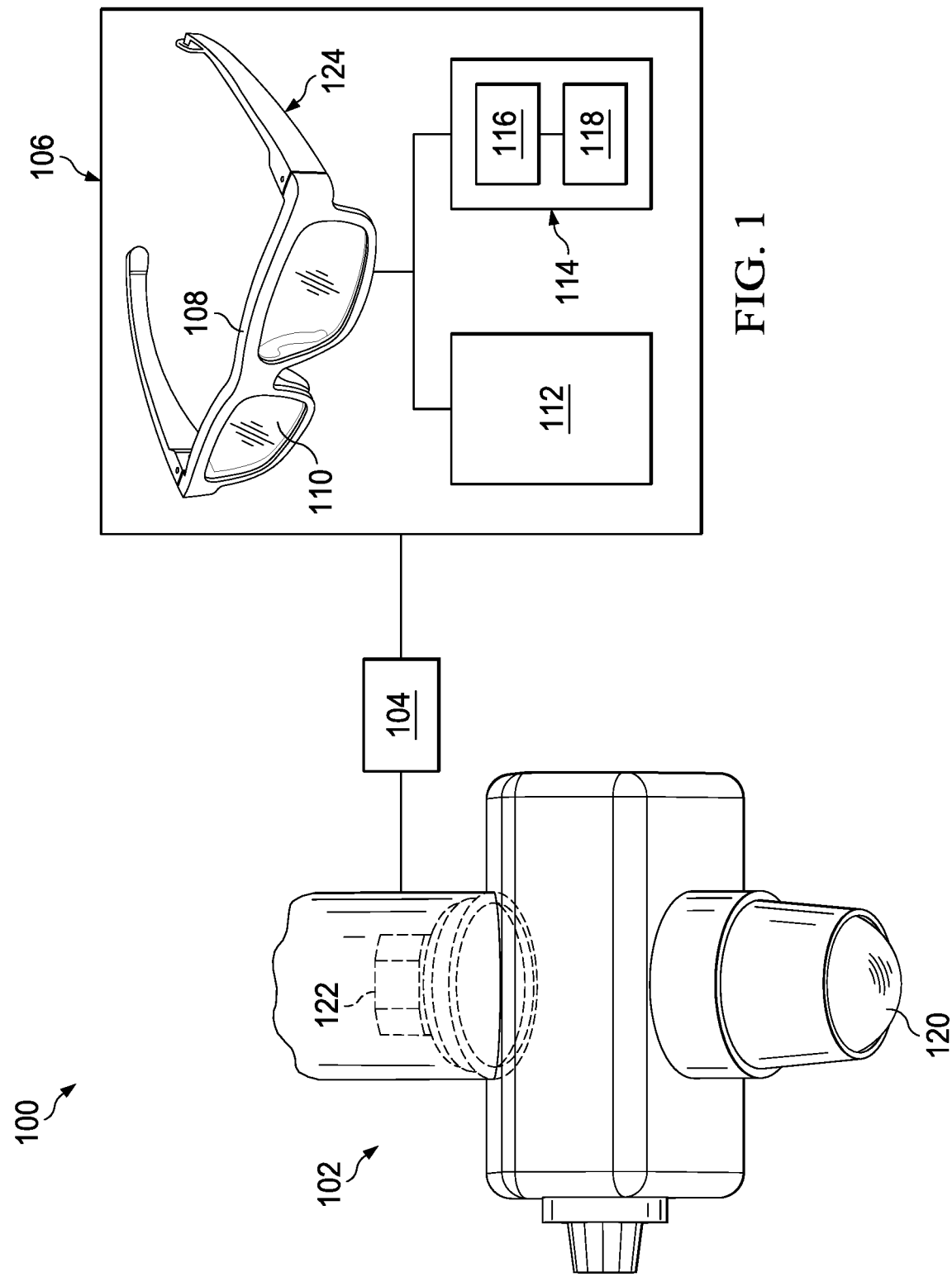
FIG. 1 is a schematic diagram of an ophthalmic surgical microscope system for performing ophthalmic surgery.

In the following description, details are set forth by way of example to facilitate discussion of the disclosed subject matter. It should be apparent to a person of ordinary skill in the field, however, that the disclosed embodiments are exemplary and not exhaustive of all possible embodiments.

The present disclosure provides systems and methods for use of augmented reality during ophthalmic surgery. In some cases, the system displays an image from an ophthalmic microscope using an augmented reality device, e.g., a headset and/or glasses. For example, augmented reality glasses may include one or more transparent or semi-transparent lenses and an optical system that projects an individual image into each eye by reflecting them from the lenses. The images are interpreted as a digital image, three-dimensional (3D) image, e.g., a hologram, that is added to the normal view of the operator through the lenses. In some cases, the digital or 3D image is semi-transparent. Thus, the projected image is visible to the operator in addition to the physical space normally viewed through the glasses. Because of the semi-transparency of the projected image, it may be difficult for an operator to see the projected image clearly with the distraction of the physical space behind the image. The system of the present disclosure may include an outer surface of a lens that may transition from transparent to opaque. For example, the outer surface may include a dimming film that is electronically controlled to transition between transparent and opaque. The outer surface may initiate a transition between transparent and opaque based on receiving a signal from a dimming system. The dimming system may include a gaze control. The gaze control may detect the gaze of an operator and determine whether an operator is focused on the projected image or the physical space. The gaze control may also detect a change in the focus of an operator from the physical space to the projected image or vice versa. When the gaze control detects a change in the focus of an operator from the physical space to the projected image, the gaze control may transmit a signal to transition the outer surface from transparent to opaque. Additionally, when the gaze control detects a change in the focus of the use from the projected image to the physical space, the gaze control may transmit a signal to transition the outer surface from opaque to transparent.

In some cases, the system and methods may be used for touchless control of operating room equipment during ophthalmic surgery. For example, the digital or 3D image projected by the augmented reality device may include virtual controls for surgical equipment. The augmented reality device may provide for tracking hands of an operator as the hands operate the surgical equipment. Further, physical devices may be utilized by the operator. For example, physical devices may include, without limitation, control knobs, handles, keyboards, and/or any other suitable physical devices appropriate for the specific implementation. In some cases, the physical devices may be disposable, such as, composed of plastic or paper. Use of virtual controls and/or physical devices, may allow operators precise control of the operating equipment without compromising sterilization.

FIG. 1 is a schematic diagram of an ophthalmic surgical microscope system 100 for performing ophthalmic surgery. Microscope system 100 includes ophthalmic microscope 102 communicatively coupled, e.g., wired or wirelessly, to imaging system 104. Imaging system 104 may be communicatively coupled, e.g., wired or wirelessly, to augmented reality device 106.

Ophthalmic microscope 102 includes at least one microscope lens 120 through which light beams reflected from an eye or associated structure pass before entering camera 122. Camera 122 may be a light field camera, video camera, or any other camera that provides digital information regarding captured images to imaging system 104. Imaging system 104 uses the digital information received from camera 122 to display an image on a visual display device, such as a multi-view display, 3D glasses or goggles, a screen, and/or any other suitable display. In some embodiments, 3D glasses may be included in augmented reality device 106 and may further be included in augmented reality glasses 124.

Microscope lens 120 may include any type of magnifying lens used in ophthalmic surgery, such as direct contact lenses and indirect lenses, including wide-view lenses. Although one microscope lens 120 is shown in FIG. 1, multiple lenses may be used to allow the magnification or other aspects of the visual image to be changed. In some embodiments, magnifying lens 120 may be present in ophthalmic microscope 102, or it may not be present at all. Particularly, because camera 122, in conjunction with imaging system 104, may change the focus of any visual image using data captured by ophthalmic microscope 102, it may be possible for the visual image displayed using imaging system 104 to be magnified without using a microscope lens 120.

Camera 122 may be any light field camera or other device or sensor able to capture information about the direction from which a light beam arrives and digitize that information. Camera 122 may capture not only image information, such as light color and intensity, but also directional information regarding the vector of the light ray. Camera 122 may include one or more photosensors that may be any electronic device able to convert light to a digital image. For example, a photosensor may be a light-to-digital sensor, a semiconductor charge-coupled device (CCD), a complementary metal-oxide-semiconductor (CMOS) device, an N-type metal-oxide-semiconductor (NMOS) device, or another electronic device containing an array of photodiodes as part of one or more integrated circuits.

Imaging system 104 may use digital information from camera 122 to produce image information and directional information. This directional information may be further used to generate a digital image and/or 3D image. Imaging system 104 may be separate from and in communication with camera 122 or may be part of camera 122. Imaging system 104 may include a processing resource that may be in communication with a memory that stores one or more algorithms for processing digital information from camera 122 to generate the information usable to display an image on a visual display, such as augmented reality glasses 124. Such algorithms may use information regarding the arrangements of components of camera 122, such as the arrangement of a photosensor, and the presence of any additional elements, in generating the information. Imaging system 104 may also use any algorithm developed for contexts other than ophthalmic surgery that is suitable for generating information usable to display a digital image and/or 3D image using augmented reality glasses 124 or any other suitable visual display. Camera 122, in connection with imaging system 104, and optionally also in connection with one or more additional cameras, photosensors, or processing resources, may produce information usable to display a digital image and/or 3D image with sufficient resolution to be used in ophthalmic surgery with augmented reality glasses 124.

Augmented reality device 106 may include augmented reality glasses 124. Augmented reality glasses 124 may include any device worn on an operator's head that is able to project different images to the left eye and right eye and to adjust the point of view of the image when the operator's head moves. Augmented reality glasses 124 include the capability to display a digital image and/or 3D image on one or more lenses 108 and can utilize positioning awareness to provide a digital reality. The digital image may consist of individual images projected onto a lens for each operator's eye. The combined digital images may be interpreted as a 3D image or hologram. The digital image and/or 3D image may be substantially transparent. Additionally, portions of augmented reality device 106 may be worn by being physically attached to person, such as via a belt, via augmented reality glasses 124, via a clip onto glasses, or by being handled by the operator, such as via looking through a computing device like a smartphone or laptop. Although augmented reality device 106 is illustrated herein using augmented reality glasses 124 as a viewing device, any viewing device may be utilized as appropriate for the particular implementation.

Augmented reality device 106 may further include outer surface 110. Outer surface 110 may be incorporated with augmented reality glasses 124, or may be a separate apparatus that is attached to augmented reality glasses 124. For example, outer surface 110 may be clipped on or otherwise coupled to lenses 108 or augmented reality glasses 124. Outer surface 110 may include a cross-polarized film or other type of film or covering that allows a transition between transparent and opaque in response to an electronic signal. When outer surface 110 transitions to opaque, outer surface 110 may emit essentially no light and may appear dark or black. Additionally, outer surface 110 may be operable to have gradations between transparent and opaque such that light may partially traverse outer surface 110.

Augmented reality device 106 may also include gaze control 112. Gaze control may be communicatively coupled, e.g., wired or wirelessly, to augmented reality glasses 124 and dimming system 114. Gaze control 112 may be any device that determines the direction and/or focus of an operator's gaze. Gaze control 112 may be operable to track an operator's eye or eyes to determine the operator's gaze. For example, gaze control 112 may be operable to determine whether an operator's eye is focused on lenses 108, which may include a projection of one or more digital images such as digital image and/or 3D image, or whether the operator's eye is focused beyond lenses 108 to physical space.

Additionally, augmented reality device 106 may include dimming system 114. Dimming system 114 may be communicatively coupled to, e.g., wired or wirelessly, augmented reality glasses 124 and/or outer surface 110. Dimming system 114 may be operable to transition outer surface 110 from transparent to opaque. The transition performed by dimming system 114 may be approximately instantaneous. Dimming system 114 may be communicatively coupled, e.g., wired or wirelessly, to gaze control 112 to receive and/or transmit signals from or to gaze control 112. For example, if gaze control 112 determines that an operator's eye is focused on a digital image projected on lenses 108, gaze control 112 may transmit a signal to dimming system 114. On receipt of the signal from gaze control 112, dimming system 114 may transition outer surface 110 to opaque. Further, if gaze control 112 determines that an operator's eye is focused on the physical space beyond the lenses 108, gaze control 112 may transmit a signal to dimming system 114. On receipt of the signal from gaze control 112, dimming system 114 may transition outer surface 110 to transparent or semi-transparent.

Dimming system 114 may include a processing resource 116 that may be in communication with a memory 118 that stores one or more algorithms for processing digital information from gaze control 112 to transition outer surface 110 between transparent and opaque. Such algorithms may use information regarding the focus and/or direction of the gaze of an operator's eye or any other suitable information specific to a particular implementation. Dimming system 114 may also use any algorithm developed for contexts other than ophthalmic surgery that is suitable for transitioning outer surface 110 between transparent and opaque.

Figure 2A:
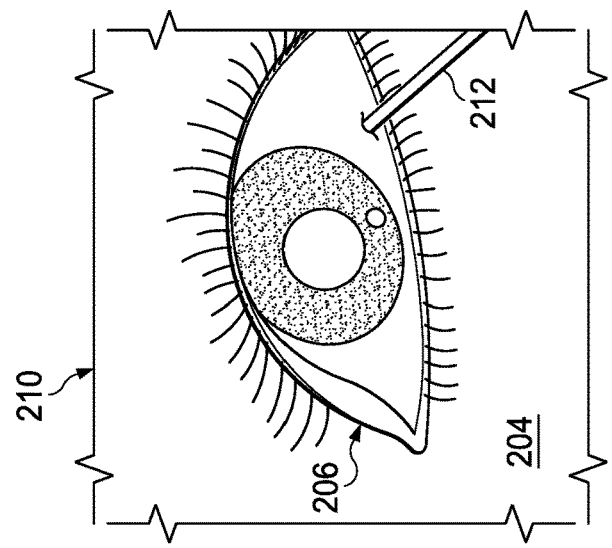
FIG. 2A illustrates a partial view using an augmented reality device where the outer surface is transparent.

FIG. 2A illustrates a partial view 202 using augmented reality device 106 where the outer surface 110 is transparent. FIG. 2A includes a partial view 202 through lenses 108 discussed with reference to FIG. 1. In the example shown in FIG. 2A, dimming system 114 may have transitioned outer surface 110 to be transparent or semi-transparent such that physical space 204 is fully or partially visible through digital image 206. For example, gaze control 112 may have detected that an operator's eye was focused or directed to physical space 204. Accordingly, gaze control 112 may have transmitted a signal to dimming system 114 and dimming system 114 may have transitioned outer surface 110 to be transparent or semi-transparent. Partial view 202 shows an exemplary view of an augmented reality environment where lenses 108 of an augmented reality device 106 are positioned within the field of vision of a operator without obscuring the entirety of the operator's view of the actual physical space 204.

Lenses 108 of an augmented reality device concurrently provide a projection of a digital image 206 within the lenses 108 and a view of actual, physical space 204 both beyond and around the projection of the digital image 206 on the lenses 108. In some embodiments, augmented reality device 106 functions in concert with imaging system 104 to establish the physical space 204 being viewed by an operator and the digital image 206 to be shown on the lenses 108. Notably, the size and scope of the digital image 206 on lenses 108 is not limited to a particular portion of an operator's field of vision as digital image 206 may extend throughout the operator's field of vision. In some embodiments, digital image 206 may be limited to predetermined viewing dimensions. In some embodiments, digital image 206 may be dimensioned to fit lenses 108 so that the digital image 206 does not obscure the entire operator's field of vision. For example, the digital image 206 may extend over a portion of one of the operator's eyes field of vision while leaving the remaining eye clear to view physical space 204. Further, the projection of digital image 206 displayed on lenses 108 may be affixed to a particular airspace corresponding to a physical location. Augmented reality device 106 may display a portion or all, of a projection of the digital image 206 relative the orientation of the operator to the physical location. Augmented reality device 106 may include one or more accelerometers and/or gyroscopes to indicate movements of the operator's head. For example, if an operator is oriented towards a particular physical location digital image 206 is displayed, but digital image 206 may be removed as the operator moves to become oriented so that the physical location is not aligned with the operator.

Digital image 206 may not be limited to a particular size or position. In some embodiments, digital image 206 may be a projection of the eye during ophthalmic surgery. In some embodiments, digital image 206 may be a projection of a variety of digital content, such as physical or digital controls, two-dimensional (2D) images, video, text, executable applications, and/or any other digital content specific to a particular implementation.

In some embodiments, digital image 206 projected on lenses 108 may be operable to be engaged through physical interaction with an operator. Specifically, digital image 206 may be projected on lenses 108 and be engaged by the operator to trigger a variety of actions and results. For example, the physical touching of the physical space 204 may activate further information to appear in digital image 206, movement of a device associated with the ophthalmic surgery, and/or removal of information from digital image 206 projected on lenses 108. Augmented reality device 106 may be operable to correlate digital image 206 projected on lenses 108 with a physical location and subsequently recognize the physical interaction of an operator with that digital image 206 to produce a predetermined result.

Figure 2B:
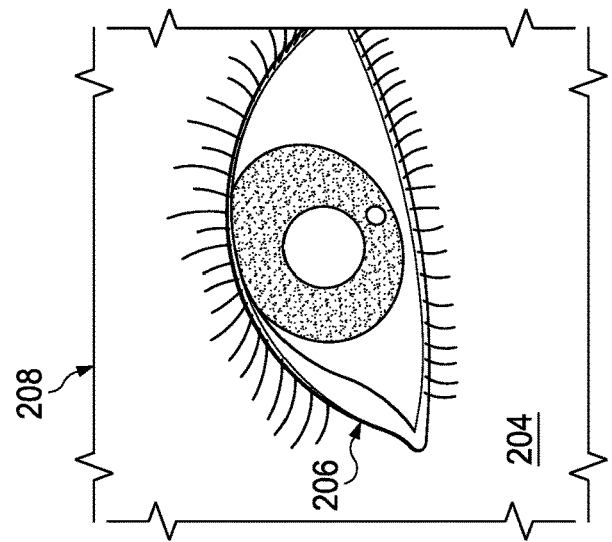
FIG. 2B illustrates a partial view using an augmented reality device where the outer surface is opaque.

FIG. 2B illustrates a partial view 208 using augmented reality device 106 where the outer surface 110 is opaque. FIG. 2B includes a partial view 208 through lenses 108 discussed with reference to FIG. 1. In the example shown in FIG. 2B, dimming system 114 may have transitioned outer surface 110 to be opaque, for example black or colorless, such that physical space 204 is fully obscured behind digital image 206. For example, gaze control 112 may have detected that an operator's eye was focused or directed to digital image 206. Accordingly, gaze control 112 may have transmitted a signal to dimming system 114 and dimming system 114 may have transitioned outer surface 110 to be opaque. Partial view 208 shows an exemplary view of an augmented reality environment where lenses 108 of an augmented reality device 106 are positioned within the field of vision of an operator and the outer surface 1100 obscures the entirety of the operator's view of the actual physical space 204.

Figure 2C:
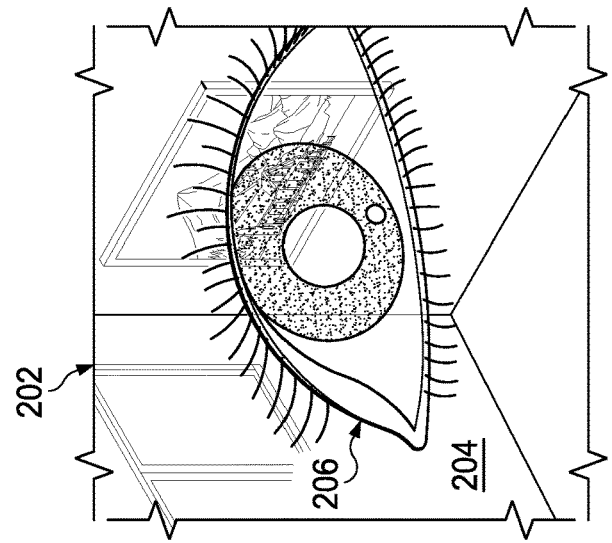
FIG. 2C illustrates a partial view using an augmented reality device where the digital image is engaged with an instrument.

FIG. 2C illustrates a partial view 210 using augmented reality device 106 where the digital image 206 is engaged with an instrument 212. FIG. 2C includes a partial view 208 through lenses 108 discussed with reference to FIG. 1. In the example shown in FIG. 2C, dimming system 114 may have transitioned outer surface 110 to be opaque, for example black or colorless, such that physical space 204 is fully obscured behind digital image 206. An operator may engage the digital image 206 with a physical or digital instrument 212 to manipulate or interact with the digital image 206. Although shown as engagement with instrument 212, engagement may also be made with an operator's appendage or another person's appendage. Augmented reality device 106 may be operable to recognize physical action by an instrument 212 or one or more other items assigned to predetermined locations within a digital space to initiate digital reactions with digital image 206. Further, engagement with digital image 206 may not in the actual physical environment, but instead may be a combination of actual physical actions by the operator and application of those actions into the augmented, digital reality by the augmented reality device 106, which is projected on the lenses 108.

Additionally, engagement with digital image 206 may be made through the use of controls or input/output devices, such as buttons, levers, a keyboard, mouse, voice-recognition control, or any other suitable controls for the particular implementation. An operator may hold or manipulate a physical control or a control on the digital image 206. A physical control may be utilized to provide the operator the tactile sensation of handling a physical device. As such, the physical controls may be disposable and may not impact the sterilization of the surgical environment. Engagement by the operator of the digital image 206 may allow for touchless control of operating equipment.

Figure 3:
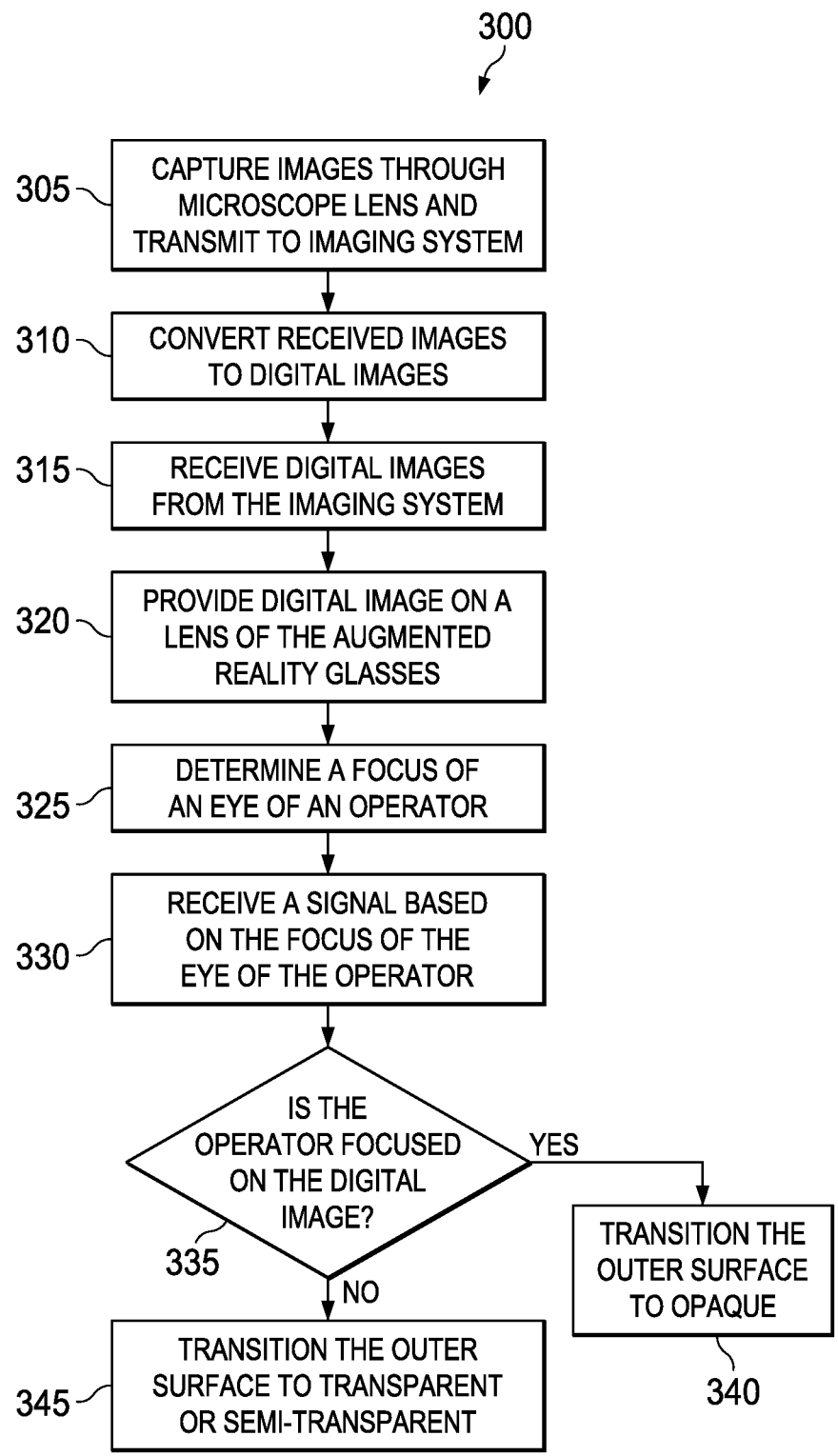
FIG. 3 illustrates a method for augmented reality ophthalmic surgical microscope projection, as described herein.

FIG. 3 illustrates a method 300 for augmented reality ophthalmic surgical microscope projection, as described herein. Method 300 may be used in conjunction with the systems and apparatus described above. Method 300 may be used to project a digital image using an augmented reality device and transition an outer surface between transparent and opaque. Certain operations described in method 300 may be optional or may be rearranged in various ophthalmic surgeries using the systems and apparatuses of this disclosure.

At step 305, an ophthalmic microscope captures images through a microscope lens and transmits the images to a camera and/or an imaging system. For example, ophthalmic microscope 102, discussed with reference to FIG. 1, may capture images using microscope lens 120.

At step 310, the camera and/or imaging system converts the received images to digital images. For example, the imaging system 104 may receive images from camera 122 and/or ophthalmic microscope 102 and convert the images into digital images.

At step 315, the augmented reality device receives the digital images. For example, imaging system 104 may transmit digital images to the augmented reality device. The augmented reality device may receive the digital images and prepare them for further processing.

At step 320, the augmented reality device projects the digital images on one or more lenses of the augmented reality glasses. For example, the digital image may be projected on lenses 108 of augmented reality glasses 124.

At step 325, the augmented reality device determines a focus or direction of an eye of an operator. For example, gaze control 112, discussed with reference to FIG. 1, may detect a gaze of an operator's eye and determine a focus or direction of the gaze. The gaze control 112 may be operable to also detect a change in the gaze, for example the focus or direction of an operator's eye.

At step 330, the augmented reality device receives a signal based on the focus of the eye of the operator. For example, the gaze control 112 may transmit a signal to the dimming system 114 that includes information regarding the focus or direction of an operator's eye. The dimming system 114 may receive the signal from the gaze control 112.

At step 335, the augmented reality device determines if the operator is focused on the digital image. For example, gaze control 112 and/or dimming system 114 may be operable to determine if the operator's eye is focused on the projected digital image, such as digital image 206 shown with reference to FIGS. 2A-2C. If the operator's eye is focused on the digital image 206, method 300 proceeds to step 340 where the dimming system 114 transitions the outer surface 110 to opaque. If the operator's eye is not focused on the digital image 206, method 300 proceeds to step 345 where the dimming system 114 transitions the outer surface 110 to transparent or semi-transparent.

The above disclosed subject matter is to be considered illustrative, and not restrictive, and the appended claims are intended to cover all such modifications, enhancements, and other embodiments which fall within the true spirit and scope of the present disclosure. For instance, any above system may include any above non-transitory computer readable medium and may carry out any above method. Any above non-transitory computer readable medium may also carry out any above method. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A system for an ophthalmic surgery comprising:
an augmented reality device communicatively coupled to an imaging system of an ophthalmic microscope, the augmented reality device comprising:
a lens configured to:
project a digital image onto an eye of an operator of the augmented reality device; and
allow the eye to view a physical space beyond the lens;
an outer surface coupled to the lens, the outer surface being at least partially transparent;
a gaze tracker comprising a device configured to:
detect a focus of the eye in order to determine the gaze of the eye;
determine if the eye is focused on the digital image or the physical space; and
transmit an indication based on the focus; and
a dimming system communicatively coupled to the gaze tracker and the outer surface, the dimming system including a processor operable to:
receive the digital image from the imaging system of the ophthalmic microscope;
project the digital image onto the lens;
receive the indication from the gaze tracker regarding the focus of the eye of the operator; and
transition the outer surface of the augmented reality device between at least partially transparent to opaque based on the received indication, the transitioning comprising:
if the eye is focused on the digital image projected onto the lens, transitioning the outer surface to opaque; and
if the eye is focused on the physical space beyond the lens, transitioning the outer surface to at least partially transparent.

2. The system of claim 1, wherein the augmented reality device comprises augmented reality glasses.

3. The system of claim 1, wherein the digital image comprises a separate image projected onto the lens for each eye of the operator.

4. The system of claim 1, further comprising an instrument configured to engage with the digital image.

5. The system of claim 4, wherein the instrument comprises a physical instrument manipulated by the operator.

6. The system of claim 4, wherein the instrument comprises a digital instrument manipulated by the operator.

7. The system of claim 1, further comprising an input/output device configured to engage with the digital image.

8. A method of performing an ophthalmic surgery comprising:
receiving a digital image from an imaging system of an ophthalmic microscope;
projecting the digital image on a lens of an augmented reality device;
detecting a focus of an eye of an operator of the augmented reality device in order to determine if the eye is focused on the digital image or a physical space beyond the lens;
receiving an indication regarding the focus of the eye of the operator; and
transitioning an outer surface of the augmented reality device between at least partially transparent to opaque based on the received indication, the transitioning comprising:
if the eye is focused on the digital image projected onto the lens, transitioning the outer surface to opaque; and
if the eye is focused on the physical space beyond the lens, transitioning the outer surface to at least partially transparent.

9. The method of claim 8, wherein the augmented reality device comprises augmented reality glasses.

10. The method of claim 8, wherein the digital image comprises a separate image projected onto the lens for each eye of the operator.

11. The method of claim 8, further comprising engaging an instrument with the digital image.

12. The method of claim 11, wherein the instrument comprises a physical instrument manipulated by the operator.

13. The method of claim 11, wherein the instrument comprises a digital instrument manipulated by the operator.

14. The method of claim 8, further comprising an input/output device configured to engage with the digital image.

15. A non-transitory computer readable medium having instructions stored therein, the instructions readable by a processor and, when read and executed, configured to cause the processor to:
receive a digital image from an imaging system of an ophthalmic microscope;
project the digital image on a lens of an augmented reality device;
determine a focus of an eye of an operator of the augmented reality device in order to determine if the eye is focused on the digital image or a physical space beyond the lens;
receive an indication regarding the focus of the eye of the operator; and
transition an outer surface of the augmented reality device between at least partially transparent to opaque based on the received indication, the transitioning comprising:
if the eye is focused on the digital image projected onto the lens, transitioning the outer surface to opaque; and
if the eye is focused on the physical space beyond the lens, transitioning the outer surface to at least partially transparent.

16. The non-transitory computer readable medium of claim 15, wherein the augmented reality device comprises augmented reality glasses.

17. The non-transitory computer readable medium of claim 15, wherein the digital image comprises a separate image projected onto the lens for each eye of the operator.

18. The non-transitory computer readable medium of claim 15, wherein the processor is further configured to engage an instrument with the digital image.

19. The non-transitory computer readable medium of claim 18, wherein the instrument comprises a physical instrument manipulated by the operator.

20. The non-transitory computer readable medium of claim 18, wherein the instrument comprises a digital instrument manipulated by the operator.

* * * * *